United States Patent [19]

Poschel et al.

[11] 4,232,021

[45] Nov. 4, 1980

[54] ANTI-DEPRESSANT METHODS

[75] Inventors: Bruno P. H. Poschel, Ann Arbor; Donald R. Maxwell, Pinckney, both of Mich.

[73] Assignee: Kefalas A/S, Copenhagen-Valby, Denmark

[21] Appl. No.: 6,317

[22] Filed: Jan. 25, 1979

[51] Int. Cl.$^2$ ............................................. A61K 31/495
[52] U.S. Cl. .................................................... 424/250
[58] Field of Search ......................................... 424/250

[56] References Cited

U.S. PATENT DOCUMENTS 3,681,346   8/1972   Petersen et al. ..................... 424/250

*Primary Examiner*—Stanley J. Friedman
*Attorney, Agent, or Firm*—Gordon W. Hueschen

[57] ABSTRACT

Pharmaceutical compositions comprising essentially pure trans-9-[3-(4-hydroxyethyl-1-piperazinyl)-propylidene]-2-trifluoromethylthiaxanthene or pharmaceutically acceptable acid addition salts thereof and a pharmaceutical carrier and methods for treating depression which comprises administering said pharmaceutical compositions.

4 Claims, No Drawings

ANTI-DEPRESSANT METHODS

BACKGROUND OF THE INVENTION

Pharmaceutical compositions comprising mixtures of cis-9-[3-(4-hydroxyethyl-1-piperazinyl)propylidene]-2-trifluromethylthiaxanthene and trans-9-[3-(4-hydroxyethyl-1-piperazinyl)propylidene]-2-trifluromethylthiaxanthene, generally referred to as flupenthixol, have been employed as neuroleptic agents, primarily in the treatment of schizophrenic patents. The decanoic acid ester of cis-9-[3-(4-hydroxyethyl-1-piperazinyl)propylidene]-2-trifluromethylthiaxanthene has been employed as a neuroleptic agent having a prolonged effect when compared to the non-esterified cis isomer component of flupenthixol. In addition, flupenthixol has also been reported to exhibit a certain degree of antidepressant activity. Those skilled in the art have attributed the anti-schizophrenic activity exclusively to the cis isomer, also termed as α-isomer, component of flupenthixol (E. C. Johnstone, et al. The Lancet, Apr. 22, 1978, 848 and T. J. Crow and E. C. Johnstone, British Journal of Pharmacology 59:466P, March, 1977). Others skilled in the art spoke in more general terms stating the following, "This study has confirmed the previous findings with thioxanthenes, that the stereoisomeric configuration is of decisive importance for the pharmacological activity (Møller-Nielsen, et al. 1962). α-Flupenthixol was found largely equipotent with flupenazine, while β-flupenthixol showed a very low activity" and it is generally believed today that any significant biological activity attributed to flupenthixol is contributed by the α-isomer, that is the compound of flupenthixol having the cis - configuration. U.S. Pat. No. 3,681,346 issued Aug. 1, 1972, describes the β-isomer as the inactive isomer in addition to giving a method for preparing it in a relatively pure form.

SUMMARY OF THE INVENTION

According to the present invention, it has now suprisingly been found that the β-isomer component of the two compounds comprising flupenthixol and pharmaceutically acceptable salts thereof, that is trans-9-[3-(4-hydroxyethyl-1-piperazinyl) propylidene]-2-trifluoromethylthiaxanthene and pharmaceutically acceptable salts thereof show activity in animal tests indicative of antidepressant activity and that the α-isomer in the screen, exhibits only nominal activity. This discovery is of special significance, since the α-isomer has a wide range of biological activities and its presence in a composition intended for use as an antidepressant could result in the composition having certain undesirable side effects at high doses.

The term "pharmaceutically acceptable salts" is intended to include salts such as the hydrochloride, sulfate, phosphate, acetate, citrate, etc.

The pharmaceutical compositions of this invention, which are useful as antidepressants in mammals, such as dogs, cats, etc., may be administered in a dose range of about 0.0036 mg. to about 0.71 mg. per kg. of body weight per day. Thus, over a 24 hour period a subject of about 70 kg. body weight would receive divided doese totalling about 0.25 mg. to about 50 mg., perferably 0.5 mg. to 20 mg., of trans-9-[3-(4-hydroxyethyl-1-piperazinyl)propylidene]-2-trifluoromethylthiaxanthene.

The pharmaceutical compositions may also contain other relatively non-toxic antidepressants, such as imipramine, amitriptyline, desipramine, doxepin used in a dose range so as to deliver about 50 mg. to 500 mg. to a 70 kg. adult over a 24 hour period or nortriptyline used in a dose range so as to deliver about 25 mg. to 300 mg. to a 70 kg. abult over a 24 hour period. In addition, such compositions may also contain relatively non-toxic tranquilizers, such as chlordiazepoxide used in a dose range so as to deliver about 5 mg. to about 50 mg. to a 70 kg. adult over a 24 hour period.

The compounds of the present invention in the described dosages are intended to be administered orally; however, other routes such as rectally and parenterally may be employed.

The active compounds of the present invention are orally administered, for example, with an inert diluent or with an assimilable edible carrier, or they may be enclosed in hard or soft gelatin capsules, or they may be compressed into tablets, or they may be incorporated directly with the food of the diet. For oral therapeutic administration, the active compounds of this invention may be incorporated with excipients and used in the form of tablets, troches, capsules, elixirs, suspensions, syrups, wafers, chewing gum, and the like. Such compositions and preparations should contain at least 0.1% of active compound. The percentage in the compositions and preparations may, of course, be varied and may conveniently be between about 5% to about 75% or more of the weight of the unit. The amount of active compound in such therapeutically useful compositions or preparations is such that a suitable dosage will be obtained. Preferred compositions or preparations according to the present invention are prepared so that an oral dosage unit form contains between about 0.1 and 50 mg. of trans-9-[3-(4-hydroxyethyl-1-piperazinyl)propylidene]-2-trifluoromethylthiaxanthene.

The tablets, troches, pills, capsules and the like may also contain the following: a binder such as gum tragacanth, acacia, corn starch or gelatin; an excipient such as dicalcium phosphate, a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain in addition to materials of the above type a liquid carrier such as a fatty oil. Various other materials may be present as coatings or to otherwise modify the physical form of the dosage unit, for instance, tablets, pills or capsules may be coated with shellac, sugar or both. A syrup or elixir may contain the active compounds, sucrose as a sweetening agent, methyl and propyl parabens as preservatives, a dye and a flavoring such as cherry or orange flavor. Of course, any material used in preparing any dosage unit form should be pharmaceutically pure and substantially non-toxic in the amounts employed.

The method for determining the anti-depressant activity is essentially the procedure described in B.P.H. Poschel and F. W. Ninteman, Life Sciences 3, 903–10 (1964) except that the electrodes are inserted in one group of rats in the dorsal raphe area and in another group of rats in the medial forebrain bundle. The test is described below.

Eight naive rats are employed in this test with four of the rats having dorsal raphe area electrodes, and four medial forebrain bundle electrodes. First, the rats are trained to self-stimulate, namely; to press a lever for the strong reward elicited by 50 μA brain stimulation. Then, prior to drug testing the rats are trained in low baseline rates of self-stimulation through the following procedure. In successive training sessions the brain stimulating current is reduced in steps to a level moderately above the reward threshold. This causes self-stimulation rates to decrease correspondingly because weaker reward is elicited. Each rat has its own final current setting, but between all rats these final current levels range from 15-25 μA. Practice sessions are run every 2 or 3 days until the rats stablize their self-stimulation rates under the reduced current levels. The slow response generated by these conditions serves as the behavioral baselines in the ensuing drug tests.

All drugs are dissolved in water and administered by oral intubation 1 hr into the self-stimulation session. Each rat is tested under all of the following treatments: hydrochloride of the cis component of flupenthixol 0.0312, 0.0625, and 0.125 mg/kg; hydrochloride of the trans component of flupenthixol 2.5, 5.0, 10.0, and 20.0 mg/kg; and water. The rats' body weights range from about 444-605 g at the time of the tests and separate drug tests on a given rat are spaced 4-7 days apart.

The trans compound of flupenthixol facilitated the rate of self-stimulation elicited from both areas of the brain with optimal dosages of 5 mg to 10 mg via oral administration. These suprising and unexpected findings clearly show that the trans component of flupenthixol has antidepressant properties.

The cis component of flupenthixol appeared to be totally inactive in the above antidepressant test.

Thus it has been shown (1) the trans component of flupenthixol is an effective antidepressant (2) by removing the corresponding cis isomer from the mixture, the anti-depressant efficiency of the remaining material (trans component of flupenthixol) is appreciably increased on a weight basis and (3) the very undesirable neuroleptic and neurological side effects (extra-pyramidal and tardive dyskinesia) of the cis component flupenthixol are entirely removed. Due to the relatively low order of toxicity associated with the trans component of flupenthixol and the removal of the highly neuroleptic cis component, the use of much higher doses in the treatment of depression when employing the pure trans isomer is permitted.

The following examples further illustrate the invention.

EXAMPLE 1

| Ingredient | Quantity |
| --- | --- |
| Trans-4-[3-[2-(trifluoromethyl)-9H-thioxanthen-9-ylidene]-propyl]-1-piperazineethanol dihydrochloride (trans-9-[3-(4-hydroxyethyl)-1-propylidene]-2-trifluoromethyl-thiaxanthene dihydrochloride) | 175g |
| Lactose | 1099g |
| Corn Starch | 39g |
| Hydroxypropyl cellulose | 30g |
| Magnesium Stearate | 7g |
| Ethanol-water 50:50 | qs |

The Trans-4-[3-[2-(trifluoromethyl)-9H-thioxanthen-9-ylidene]-propyl]-1-piperazineethanol dihydrochloride, lactose and hydroxypropyl cellulose are blended and granulated with 50:50 ethanol-water. The wet granulation is screened, dried and rescreened. The resulting dried granulation is blended with the magnesium stearate and the corn starch, and the mixture is compressed into 225 mg., tablets using 11/32 inch standard concave punches. Yield equals approximately 6000 tablets, each containing 29.2 mg. of Trans-4-[3-[2-(trifluoromethyl)-9H-thioxanthen-9-ylidene]-propyl]-1-piperazineethanol dihydrochloride equivalent to 25 gm. of Trans-4-[3-[2-(trifluoromethyl)-9H-thioxanthen-9-ylidene]-propyl]-1-piperazineethanol base.

By substituting an equivalent amount of another pharmaceutically acceptable Trans-4-[3-[2-(trifluoromethyl)-9H-thioxanthen-9-ylidene]-propyl]-1-piperazineethanol salt for the Trans-4-[3-[2-(trifluoromethyl)-9H-thioxanthen-9-ylidene]-propyl]-1-piperazineethanol dihydrochloride and adjusting the amount of lactose to give the same total weight in the above formula, there are again obtained 225 mg. tablets each containing the equivalent of 25 mg. of Trans-4-[3-[2-(trifluoromethyl)-9H-thioxanthen-9-ylidene]-propyl]-1-piperazineethanol base.

EXAMPLE 2

| Ingredient | Quantity |
| --- | --- |
| Trans-4-[3-[2-(trifluoromethyl)-9H-thioxanthen-9-xylidene]-propl]-1-piperazineethanol dihydrochloride | 17.5g |
| Lactose | 1246.5g |
| Corn Starch | 39g |
| Hydroxypropyl cellulose | 30g |
| Magnesium Stearate | 7g |
| Ethanol-water 50:50 | qs |

The Trans-4-[3-[2-(trifluoromethyl)-9H-thioxanthen-9-ylidene]-propyl]-1-piperazineethanol dihydrochloride, lactose and hydroxypropyl cellulose are blended and granulated with 50:50 ethanol-water. The wet granulation is screened, dried and rescreened. The resulting dried granulation is blended with the magnesium stearate and the corn starch, and the mixture is compressed into 225 mg., tablets using 11/32 inch standard concave punches. Yield equals approximately 6000 tablets, each containing 2.92 mg. of Trans-4-[3-[2-(trifluoromethyl)-9H-thioxanthen-9-ylidene]-propyl]-1-piperazineethanol dihydrochloride equivalent to 2.5 mg. of Trans-4-[3-[2-(trifluoromethyl)-9H-thioxanthen-9-ylidene]-propyl]-1-piperazineethanol base.

By substituting an equivalent amount of another pharmaceutically acceptable Trans-4-[3-[2-(trifluoromethyl)-9H-thioxanthen-9-ylidene]-ylidene]-propyl]-1-piperazineethanol salt for the Trans-4-[3-[2-(trifluoromethyl)-9H-thioxanthen-9-ylidene]-propyl]-1-piperazineethanol dihydrochloride and adjusting the amount of lactose to give the same total weight in the above formula, there are again obtained 225 mg. tablets each containing the equivalent of 2.5 mg. of Trans-4-[3-[2-(trifluoromethyl)-9H-thioxanthen-9-ylidene]-propyl]-1-piperazineethanol base.

EXAMPLE 3

| Ingredient | Quantity |
| --- | --- |
| Trans-4-[3-[2-(trifluoromethyl)-9H-thioxanthen-9-ylidene]-propyl]-1-piperazineethanol dihydrochloride | 7g |
| Lactose | 1267g |
| Corn Starch | 39g |

| Ingredient | Quantity |
| --- | --- |
| Hydroxypropyl cellulose | 30g |

The Trans-4-[3-[2-(trifluoromethyl)-9H-thioxanthen-9-ylidene]-propyl]-1-piperazineethanol dihydrochloride, lactose and hydroxypropyl cellulose are blended and granulated with 50:50 ethanol-water. The wet granulation is screened, dried and rescreened. The resulting dried granulation is blended with the magnesium stearate and the corn starch, and the mixture is compressed into 225 mg., tablets using 11/32 inch standard concave punches. Yield equals approximately 6000 tablets, each containing 1.17 mg. of Trans-4-[3-[2-(trifluoromethyl)-9H-thioxanthen-9-ylidene]-propyl]-1-piperazineethanol dihydrochloride equivalent to 1.0 mg. of Trans-4-[3-[2-(trifluoromethyl)-9H-thioxanthen-9-ylidene]-propyl]-1-piperazineethanol base.

By substituting an equivalent amount of another pharmaceutically acceptable Trans-4-[3-[2-(trifluoromethyl)-9H-thioxanthen-9-ylidene]-1-piperazineethanol salt for the Trans-4-[3-[2-(trifluoromethyl)-9H-thioxanthen-9-ylidene]-propyl]-1-piperazineethanol dihydrochloride and adjusting the amount of lactose to give the same total weight in the above formula, there are again obtained 225 mg. tablets each containing the equivalent of 1.0 mg. of Trans-4-[3-[2-(trifluoromethyl)-9H-thioxanthen-9-ylidene]-propyl]-1-piperazineethanol base.

EXAMPLE 4

| Ingredient | Quantity |
| --- | --- |
| Trans-4-[3-[2-(trifluoromethyl)-9H-thioxanthen-9-ylidene]-propyl]-1-piperazineethanol dihydrochloride | 350g |
| Lactose | 924g |
| Corn Starch | 39g |
| Hydroxypropyl cellulose | 30g |
| Magnesium Stearate | 7g |
| Ethanol-water 50:50 | qs |

The Trans-4-[3-[2-(trifluoromethyl)-9H-thioxanthen-9-ylidene]-propyl]-1-piperazineethanol dihydrochloride, lactose and hydroxypropyl cellulose are blended and granulated with 50:50 ethanol-water. The wet granulation is screened, dried and rescreened. The resulting dried granulation is blended with the magnesium stearate and the corn starch and the mixture is compressed into 225 mg. tablets using 11/32 inch standard concave punches. Yield equals approximately 6000 tablets, each containing 58.4 mg. of Trans-4-[3-[2-(trifluoromethyl)-9H-thioxanthen-9-ylidene]-propyl]-1-piperineethanol dihydrochloride equivalent to 50. mg. of Trans-4-[3-[2-(trifluoromethyl)-9H-thioxanthen-9-ylidene]-propyl]-1-piperazineethanol base.

By substituting an equivalent amount of another pharmaceutically acceptable Trans-4-[3-[2-(trifluoromethyl)-9H-thioxanthen-9-ylidene]-propyl]-1-piperazineethanol salt for the Trans-4-[3-[2-(trifluoromethyl)-9H-thioxanthen-9-ylidene]-propyl]-1-piperazineethanol dihydrochloride and adjusting the amount of lactose to give the same total weight in the above formula, there are again obtained 225 mg. tablets each containing the equivalent of 50 mg. of Trans-4-[3-[2-(trifluoromethyl)-9H-thioxanthen-9-yliden]-propyl]-1-piperazineethanol base.

EXAMPLE 5

| Ingredient | Quantity |
| --- | --- |
| Trans-4-[3-[2-(trifluoromethyl)-9H-thioxanthen-9-ylidene]-propyl]-1-piperazineethanol dihydrochloride | 292g |
| Lactose | 1681g |
| Magnesium stearate | 27g |

The mixture is blended and filled into No. 4 hard gelatin capsules, filling each capsule with 200 mg. of the powder mixture. Yield equals approximately 10,000 capsules each containing 29.2 mg. of Trans-4-[3-[2-(trifluoromethyl)-9H-thixoanthen-9-ylidene]-propyl]-1-piperazineethanol dihydrochloride equivalent to 25 mg. of Trans-4-[3-[2-(trifluoromethyl)-9H-thioxanthen-9-ylidene]-propyl]-1-piperazineethanol base.

By substituting an equivalent amount of another pharmaceutically acceptable salt of Trans-4-[3-[2-(trifluoromethyl)-9H-thioxanthen-9-ylidene]-propyl]-1-piperazineethanol for the Trans-4-[3-[2-(trifluoromethyl)-9H-thioxanthen-9-ylidene]-propyl]-1-piperazineethanol dihydrochloride and adjusting the amount of lactose to give the same total weight in the above formula, there are again obtained 200 mg. capsules, each containing the equivalent of 25 mg. of Trans-4-[3-[2-(trifluoromethyl)-9H-thioxanthen-9-ylidene]-propyl]-1-piperazineethanol base.

EXAMPLE 6

| Ingredient | Quantity |
| --- | --- |
| Trans-4-[3-[2-(trifluoromethyl)-9H-thioxanthen-9-ylidene]-propyl]-1-piperazineethanol dihydrochoride | 29.2g |
| Lactose | 1944.g |
| Magnesium stearate | 27g |

The mixture is blended and filled into No. 4 hard gelatin capsules, filling each capsule with 200 mg. of the powder mixture. Yield equals approximately 10,000 capsules each containing 2.92 mg. of Trans-4-[3-[2-(trifluoromethyl)-9H-thioxanthen-9-ylidene]-propyl]-1-piperazineethanol dihydrochloride equivalent to 2.5 mg. of Trans-4-[3-[2-(trifluoromethyl)-9H-thioxanthen-9-ylidene]-propyl]-1-piperazineethanol base.

By substituting an equivalent amount of another pharmaceutically acceptable salt of Trans-4-[3-[2-(trifluoromethyl)-9H-thioxanthen-9-ylidene]-propyl]-1-piperazineethanol for the Trans-4-[3-[2-(trifluoromethyl)-9H-thioxanthen-9-ylidene]-propyl]-1-piperazineethanol dihydrochloride and adjusting the amount of lactose to give the same total weight in the above formula, there are again obtained 200 mg. capsules, each containing the equivalent of 2.5 mg. of Trans-4-[3-[2-(trifluoromethyl)-9H-thioxanthen-9-ylidene]-propyl]-1-piperazineethanol base.

EXAMPLE 7

| Ingredient | Quantity |
| --- | --- |
| Trans-4-[3-[2-(trifluoromethyl)-9H-thioxanthen-9-ylidene]-propyl]- | |

| Ingredient | Quantity |
| --- | --- |
| 1-piperazineethanol dihydrochoride | 11.7g |
| Lactose | 1961.5g |
| Magnesium stearate | 27g |

The mixture is blended and filled into No. 4 hard gelatin capsules, filling each capsule with 200 mg. of the power mixture. Yield equals approximately 10,000 capsules each containing 1.17 mg. of Trans-4-[3-[2-(trifluoromethyl)-9H-thioxanthen-9-ylidene]-propyl]-1-piperazineethanol dihydrochloride equivalent to 1.0 mg. of Trans-4-[3-[2-(trifluoromethyl)-9H-thioxanthen-9-ylidene]-propyl]-1-piperazineethanol base.

By substituting an equivalent amount of another pharmaceutically acceptable salt of Trans-4-[3-[2-(trifluoromethyl)-9H-thioxanthen-9-ylidene]-propyl]-1-piperazineethanol for the Trans-4-[3-[2-(trifluoromethyl)-9H-thioxanthen-9-ylidene]-propyl]-1-piperazineethanol dihydrochloride and adjusting the amount of lactose to give the same total weight in the above formula, there are again obtained 200 mg. capsules, each containing the equivalent of 1.0 mg. of Trans-4-[3-[2-(trifluoromethyl)-9H-thioxanthen-9-ylidene]-propyl]-1-piperazineethanol base.

EXAMPLE 8

| Ingredient | Quantity |
| --- | --- |
| Trans-4-[3-[2-(trifluoromethyl)-9H-thioxanthen-9-ylidene]-propyl]-1-piperazineethanol dihydrochloride | 584g |
| Lactose | 1389g |
| Magnesium stearate | 27g |

The mixture is blended and filled into No. 4 hard gelatin capsules, filling each capsule with 200 mg. of the powder mixture. Yield equals approximately 10,000 capsules each containing 58.4 mg. of Trans-4-[3-[2-(trifluoromethyl)-9H-thioxanthen-9-ylidene]-propyl]-1-piperazineethanol dihydrochloride equivalent to 50 mg. of Trans-4-[3-[2-(trifluoromethyl)-9H-thioxanthen-9-ylidene]-propyl]-1-piperazineethanol base.

By substituting an equivalent amount of another pharmaceutically acceptable salt of Trans-4-[3-[2-(trifluoromethyl)-9H-thioxanthen-9-ylidene]-propyl]-1-piperazineethanol for the Trans-4-[3-[2-(trifluoromethyl)-9H-thioxanthen-9-ylidene]-propyl]-1-piperazineethanol dihydrochloride and adjusting the amount of lactose to give the same total weight in the above formula, there are again obtained 200 mg. capsules, each containing the equivalent of 50 mg. of Trans-4-[3-[2-(trifluoromethyl)-9H-thioxanthen-9-ylidene]-propyl]-1-piperazineethanol base.

EXAMPLE 9

| Ingredient | Quantity |
| --- | --- |
| Trans-4-[3-[2-(trifluoromethyl)-9H-thioxanthen-9-ylidene]-propyl]-1-piperazineethanol dihydrochloride | 1.17mg |
| Phemerol Chloride Recrystallized | 0.1mg |
| Water for Injection USP | qs ad 1.0ml |

The Trans-4-[3-[2-(trifluoromethyl)-9H-thioxanthen-9-ylidene]-propyl]-1-piperazineethanol dihydrochloride is mixed with about two-thirds of the required volume of Water for Injection USP followed by the addition of Phemerol Chloride followed by the addition of sufficient Water for Injection to reach the desired volume. After mixing, the solution is sterilized by membrane filtration (a 0.22 micron Milliter filter membrane represents a suitable filter). The desired quantity of above prepared solution is filled into appropriate size multiple dose vials suitable for injection preparations and stopper with gun rubber or suitable butyl rubber closures and sealed with aluminum ferrules. The preparation may also be filled into suitable size single dose glass ampoules sealed.

Using the above procedure, solutions containing 1.17, 2.92, 5.85 or 11.17 mg./ml of Trans-4-[3-[2-(trifluoromethyl)-9H-thioxanthen-9-ylidene]-propyl]-1-piperazineethanol dihydrochloride may be prepared, giving a formulation with the equivalent amount of Trans-4-[3-[2-(trifluoromethyl)-9H-thioxanthen-9-ylidene]-propyl]-1-piperazineethanol per ml. of solution, 1 mg., 2.5 mg., 5.0 mg., 10.0 mg., respectively.

We claim:

1. A method for treating depression in mammals which comprises administering an effective anti-depressant amount of trans-9-[3(4-hydroxyethyl-1-piperazinyl)-propylidene]-2-trifluoromethylthiaxanthene or a pharmaceutically acceptable acid addition salt thereof, essentially free from its cis isomer.

2. A method for treating depression in mammals which comprises administering an antidepressant pharmaceutical composition comprising from 0.1 mg. to 50 mg. of trans-9-[3-(4-hydroxyethyl-1-piperazinyl)-propylidene]-2-trifluoromethylthiaxanthene or a pharmaceutically acceptable acid addition salt thereof, essentially free from its cis isomer.

3. A method for treating depression in mammals which comprises administering 0.0036 mg. to 0.71 mg. per kg of body weight per day of a compound of claim 2.

4. A method for treating depression in mammals which comprises administering the composition of claim 2 wherein said compound is in the form of its dihydrochloride salt.

* * * * *

UNITED STATES PATENT AND TRADEMARK OFFICE
CERTIFICATE OF CORRECTION

PATENT NO. : 4,232,021                               Page 1 of 2

DATED      : November 4, 1980

INVENTOR(S) : Bruno P. H. Poschel and Donald R. Maxwell

It is certified that error appears in the above-identified patent and that said Letters Patent are hereby corrected as shown below:

Col. 1, line 62; "doese" should read -- doses --
Col. 2, line 5; "abult" should read -- adult --
Col. 4, line 5; "25 gm." should read -- 25 mg. --
Col. 4, line 25; "propl]-" should read -- propyl]- --
Col. 4, lines 50 & 51; "-9-ylidene]-ylidene]-propyl]-" should read
  -- -9-ylidene]-propyl]- --
Col. 5, line 23; "-9-ylidene]-1-" should read -- -9-ylidene]-propyl]-1- --
Col. 5, line 56; "-piperineethanol" should read -- -piperazineethanol --
Col. 6, line 18; "-9H-thixoanthen-9-" should read -- -9H-thioxanthen-9- --
Col. 6, lines 25 & 26 and lines 55 & 56; "[2-(trifluorome-    should be
                                            thyl)-"          hyphenated
  -- [2-(thifluoro-
     methyl)- --
Col. 6, lines 26 & 27 and lines 56 & 57; "-1-piperazinee-    should be
                                            thanol"         hyphenated
  -- -1-piperazine-
     ethanol --
Col. 7, lines 20 & 21 and lines 50 & 51; "[2-(trifluorome-   should be
                                            thyl)-"         hyphenated
  -- [2-(trifluoro-
     methyl)- --

UNITED STATES PATENT AND TRADEMARK OFFICE
CERTIFICATE OF CORRECTION

PATENT NO. : 4,232,021

DATED : November 4, 1980

INVENTOR(S) : Bruno P. H. Poschel and Donald R. Maxwell

It is certified that error appears in the above-identified patent and that said Letters Patent are hereby corrected as shown below:

Col. 7, lines 21 & 22 and lines 51 & 52; "-1-piperazinee-thanol" should be hyphenated -- -1-piperazine-ethanol --

Col. 8, line 19; "Milliter" should read -- Millipore --

Col. 28 & 29; "[2-(trifluorome-thyl)-" should be hyphenated -- [2-(trifluoromethyl)- --

Col. 29 & 30; "-1-piperazinee-thanol" should be hyphenated -- -1-piperazine-ethanol --

Signed and Sealed this

Twenty-first Day of April 1981

[SEAL]

Attest:

RENE D. TEGTMEYER

Attesting Officer    Acting Commissioner of Patents and Trademarks